United States Patent
Newton et al.

(10) Patent No.: US 7,357,792 B2
(45) Date of Patent: Apr. 15, 2008

(54) POSITIVE PUSH MEDICAL VALVE WITH INTERNAL SEAL

(75) Inventors: Brian L. Newton, Woonsocket, RI (US); Andrew L. Cote, Sr., Merrimack, NH (US)

(73) Assignee: Nypro Inc., Clinton, MA (US)

( * ) Notice: Subject to any disclaimer, the term of this patent is extended or adjusted under 35 U.S.C. 154(b) by 206 days.

(21) Appl. No.: 10/687,515

(22) Filed: Oct. 16, 2003

(65) Prior Publication Data

US 2004/0133171 A1    Jul. 8, 2004

Related U.S. Application Data

(60) Provisional application No. 60/422,074, filed on Oct. 29, 2002.

(51) Int. Cl.
*A61M 39/00* (2006.01)

(52) U.S. Cl. .................. 604/244; 604/247; 604/256

(58) Field of Classification Search ............ 604/99.04, 604/246, 207, 206, 205, 202, 244, 256, 200, 604/201, 247; 251/149, 149.1
See application file for complete search history.

(56) References Cited

U.S. PATENT DOCUMENTS

| | | | |
|---|---|---|---|
| 2,594,405 A | 4/1952 | Deters | 137/53 |
| 2,693,801 A | 11/1954 | Foreman | 128/214 |
| 2,705,501 A | 4/1955 | Frizsch et al. | 137/113 |
| 2,756,740 A | 7/1956 | Deane | 128/1 |
| 2,899,975 A | 8/1959 | Fernandez | 137/543.17 |
| 2,999,499 A | 9/1961 | Willett | 128/214 |
| 3,087,492 A | 4/1963 | Garth | 128/350 |
| 3,105,511 A | 10/1963 | Murphy, Jr. | 137/399 |
| 3,192,949 A | 7/1965 | De See | 137/540 |
| 3,385,301 A | 5/1968 | Harautuneian | 128/349 |
| 3,399,677 A | 9/1968 | Gould et al. | 128/349 |
| 3,416,567 A | 12/1968 | Von Dardel et al. | 137/604 |
| 3,506,005 A | 4/1970 | Gilio et al. | 128/214 |
| 3,538,950 A | 11/1970 | Porteners | 137/608 |
| 3,570,484 A | 3/1971 | Steer | 128/214 |
| 3,572,375 A | 3/1971 | Rosenberg | 137/512 |

(Continued)

FOREIGN PATENT DOCUMENTS

EP    0268480 A1    5/1988

(Continued)

*Primary Examiner*—Nicholas D. Lucchesi
*Assistant Examiner*—Melissa A. McCorkle
(74) *Attorney, Agent, or Firm*—Bromberg & Sunstein LLP

(57) ABSTRACT

A medical valve having an open mode to permit fluid flow and a closed mode to prevent fluid flow has a body and a valving element within the interior of the body. The body also has a valving element within its interior, and a proximal port and a distal port. The valving element controls fluid flow between the proximal and distal ports. Moreover, the valving element includes a resilient member and a plug. The resilient member forms a variable sized fluid chamber within the interior of the body, while the plug cooperates with the gland to provide an internal seal (within the interior of the body) that is spaced from the proximal port. The plug is capable of radially expanding the resilient member when the valve transitions from the closed mode to the open mode. The fluid chamber has a larger volume when in the open mode than when in the closed mode.

19 Claims, 5 Drawing Sheets

U.S. PATENT DOCUMENTS

| | | | |
|---|---|---|---|
| 3,726,282 A | 4/1973 | Patel | 128/349 BV |
| 3,806,086 A | 4/1974 | Cloyd | 251/149.7 |
| 3,831,629 A | 8/1974 | Mackal et al. | 137/525 |
| 3,838,843 A | 10/1974 | Bernhard | 251/149.1 |
| 3,923,065 A | 12/1975 | Nozick et al. | 128/348 |
| 3,965,910 A | 6/1976 | Fischer | 128/349 R |
| 3,994,293 A | 11/1976 | Ferro | 128/214 R |
| 4,063,555 A | 12/1977 | Ulinder | 128/214 R |
| 4,080,965 A | 3/1978 | Phillips | 128/214 D |
| 4,094,195 A | 6/1978 | Friswell et al. | 73/422 GC |
| 4,094,196 A | 6/1978 | Friswell | 73/422 GC |
| 4,116,201 A | 9/1978 | Shah | 128/351 |
| 4,121,585 A | 10/1978 | Becker, Jr. | 128/214 R |
| 4,143,853 A | 3/1979 | Abramson | 251/149.1 |
| 4,223,808 A | 9/1980 | Williams et al. | 222/88 |
| 4,300,571 A | 11/1981 | Waldbillig | 128/673 |
| 4,324,239 A | 4/1982 | Gordon et al. | 128/214 R |
| 4,333,455 A | 6/1982 | Bodicky | 128/214.4 |
| 4,334,551 A | 6/1982 | Pfister | 137/614.03 |
| 4,344,435 A | 8/1982 | Aubin | 128/350 R |
| 4,387,879 A | 6/1983 | Tauschinski | 251/149.1 |
| 4,401,432 A | 8/1983 | Schwartz | 604/89 |
| 4,421,296 A | 12/1983 | Stephens | 251/149.7 |
| 4,458,480 A | 7/1984 | Irwin | 60/39.63 |
| 4,496,348 A | 1/1985 | Genese et al. | 604/167 |
| 4,498,658 A | 2/1985 | Mikiya | 251/149.6 |
| 4,534,758 A | 8/1985 | Akers et al. | 604/85 |
| 4,535,820 A | 8/1985 | Raines | 137/854 |
| 4,550,785 A | 11/1985 | Hibbard et al. | 173/134 |
| 4,551,136 A | 11/1985 | Mandl | 604/141 |
| 4,585,435 A | 4/1986 | Vaillancourt | 604/27 |
| 4,596,557 A | 6/1986 | Pexa | 604/86 |
| 4,611,973 A | 9/1986 | Birdwell | 417/342 |
| 4,617,015 A | 10/1986 | Foltz | 604/100 |
| 4,661,110 A | 4/1987 | Fortier et al. | 604/256 |
| 4,675,003 A | 6/1987 | Hooven | 604/9 |
| 4,681,132 A | 7/1987 | Lardner | 137/271 |
| 4,683,905 A | 8/1987 | Vigneau et al. | 137/329 |
| 4,683,916 A | 8/1987 | Raines | 137/854 |
| 4,698,061 A | 10/1987 | Makaryk et al. | 604/408 |
| 4,710,168 A | 12/1987 | Schwab et al. | 604/99 |
| 4,712,583 A | 12/1987 | Pelmulder et al. | 137/852 |
| 4,743,235 A | 5/1988 | Waldbillig et al. | 604/250 |
| 4,745,950 A | 5/1988 | Mathieu | 137/798 |
| 4,749,003 A | 6/1988 | Leason | 137/854 |
| 4,752,287 A | 6/1988 | Kurtz et al. | 604/99 |
| 4,752,292 A | 6/1988 | Lopez et al. | 604/244 |
| 4,758,224 A | 7/1988 | Siposs | 604/119 |
| 4,776,369 A | 10/1988 | Lardner et al. | 137/515.5 |
| 4,809,679 A | 3/1989 | Shimonaka et al. | 128/4 |
| 4,816,020 A | 3/1989 | Brownell | 604/97 |
| 4,819,684 A | 4/1989 | Zaugg et al. | 137/112 |
| 4,842,591 A * | 6/1989 | Luther | 604/537 |
| 4,850,978 A | 7/1989 | Dudar et al. | 604/201 |
| 4,874,377 A | 10/1989 | Newgard et al. | 604/167 |
| 4,915,687 A | 4/1990 | Sivert | 604/83 |
| 4,917,668 A | 4/1990 | Haindl | 604/167 |
| 4,935,010 A | 6/1990 | Cox et al. | 604/122 |
| 4,966,199 A | 10/1990 | Ruschke | 137/843 |
| 5,006,114 A | 4/1991 | Rogers et al. | 604/167 |
| 5,041,087 A | 8/1991 | Loo et al. | 604/83 |
| 5,048,537 A | 9/1991 | Messinger | 128/673 |
| 5,049,128 A | 9/1991 | Duquette | 604/83 |
| 5,059,175 A | 10/1991 | Hanover et al. | 604/891.1 |
| 5,065,783 A | 11/1991 | Ogle, II | 137/68.1 |
| 5,080,654 A | 1/1992 | Picha et al. | 604/167 |
| 5,085,645 A | 2/1992 | Purdy et al. | 604/167 |
| 5,100,394 A | 3/1992 | Dudar et al. | 604/283 |
| 5,108,380 A | 4/1992 | Herlitze et al. | 604/283 |
| 5,147,333 A | 9/1992 | Raines | 604/249 |
| 5,171,230 A | 12/1992 | Eland et al. | 604/250 |
| 5,199,947 A | 4/1993 | Lopez et al. | 604/56 |
| 5,201,715 A | 4/1993 | Masters | 604/175 |
| 5,203,775 A | 4/1993 | Frank et al. | 604/256 |
| 5,215,538 A | 6/1993 | Larkin | 604/249 |
| 5,221,271 A | 6/1993 | Nicholson et al. | 604/283 |
| 5,230,706 A | 7/1993 | Duquette | 604/83 |
| 5,242,393 A | 9/1993 | Brimhall et al. | 604/86 |
| 5,242,432 A | 9/1993 | DeFrank | 604/284 |
| 5,269,771 A | 12/1993 | Thomas et al. | 604/213 |
| 5,280,876 A | 1/1994 | Atkins | 251/149.1 |
| 5,300,034 A | 4/1994 | Behnke et al. | 604/167 |
| 5,320,328 A | 6/1994 | Decloux et al. | 251/326 |
| 5,330,435 A | 7/1994 | Vaillancourt | 604/167 |
| 5,349,984 A | 9/1994 | Weinheimer et al. | 137/543.21 |
| 5,360,413 A | 11/1994 | Leason et al. | 604/249 |
| 5,380,306 A | 1/1995 | Brinon | 604/244 |
| 5,390,898 A | 2/1995 | Smedley et al. | 251/149.6 |
| 5,401,255 A | 3/1995 | Sutherland et al. | 604/247 |
| 5,439,451 A | 8/1995 | Collinson et al. | 604/247 |
| 5,465,938 A | 11/1995 | Werge et al. | 251/149.1 |
| 5,474,536 A | 12/1995 | Bonaldo | 604/86 |
| 5,474,544 A | 12/1995 | Lynn | 604/283 |
| 5,509,433 A | 4/1996 | Paradis | 137/1 |
| 5,509,912 A | 4/1996 | Vaillancourt et al. | 604/283 |
| 5,520,666 A | 5/1996 | Choudhury et al. | 604/283 |
| 5,533,708 A | 7/1996 | Atkinson et al. | 251/149.1 |
| 5,533,983 A | 7/1996 | Haining | 604/249 |
| 5,535,771 A * | 7/1996 | Purdy et al. | 137/15.01 |
| 5,549,566 A | 8/1996 | Elias et al. | 604/167 |
| 5,569,209 A | 10/1996 | Roitman | 604/190 |
| 5,569,235 A | 10/1996 | Ross et al. | 604/403 |
| 5,573,516 A | 11/1996 | Tyner | 604/249 |
| 5,578,059 A | 11/1996 | Patzer | 604/249 |
| 5,616,129 A | 4/1997 | Mayer | 604/167 |
| 5,616,130 A | 4/1997 | Mayer | 604/167 |
| 5,620,434 A | 4/1997 | Brony | 604/406 |
| 5,674,206 A | 10/1997 | Allton et al. | 604/249 |
| 5,676,346 A | 10/1997 | Leinsing | 251/149.1 |
| 5,685,866 A | 11/1997 | Lopez | 604/249 |
| 5,694,686 A | 12/1997 | Lopez | 29/890.126 |
| 5,695,466 A | 12/1997 | Lopez et al. | 604/93 |
| 5,699,821 A | 12/1997 | Paradis | 137/1 |
| 5,700,248 A | 12/1997 | Lopez | 604/249 |
| 5,730,418 A | 3/1998 | Feith et al. | 251/149.6 |
| 5,749,861 A | 5/1998 | Guala et al. | 604/249 |
| RE35,841 E | 7/1998 | Frank et al. | 604/256 |
| 5,806,831 A | 9/1998 | Paradis | 251/149.1 |
| 5,820,601 A | 10/1998 | Mayer | 604/167 |
| 5,921,264 A | 7/1999 | Paradis | 137/15 |
| 6,029,946 A | 2/2000 | Doyle | 251/149.1 |
| 6,036,171 A | 3/2000 | Weinheimer et al. | 251/149.1 |
| 6,039,302 A | 3/2000 | Cote, Sr. et al. | 251/149.1 |
| 6,048,335 A | 4/2000 | Mayer | 604/167 |
| 6,050,978 A | 4/2000 | Orr et al. | 604/249 |
| 6,063,062 A | 5/2000 | Paradis | 604/249 |
| 6,068,011 A | 5/2000 | Paradis | 137/1 |
| 6,079,432 A | 6/2000 | Paradis | 137/1 |
| 6,089,541 A | 7/2000 | Weinheimer et al. | 251/149.6 |
| 6,152,900 A | 11/2000 | Mayer | 604/167 |
| 6,168,137 B1 * | 1/2001 | Paradis | 251/149.6 |
| 6,228,069 B1 | 5/2001 | Barth et al. | 604/249 |
| 6,245,048 B1 | 6/2001 | Fangrow, Jr. et al. | 604/249 |
| 6,290,206 B1 | 9/2001 | Doyle | 251/149.1 |
| 6,344,033 B1 | 2/2002 | Jepson et al. | 604/256 |
| 6,428,520 B1 | 8/2002 | Lopez et al. | 604/249 |
| 6,543,745 B1 | 4/2003 | Enerson | 251/149.7 |
| 6,595,964 B2 | 7/2003 | Finley et al. | 604/246 |
| 6,609,696 B2 | 8/2003 | Enerson | 251/86 |
| 6,669,673 B2 | 12/2003 | Lopez | 604/249 |
| 6,761,286 B2 * | 7/2004 | Py et al. | 222/105 |
| 2003/0050610 A1 | 5/2003 | Newton et al. | 604/256 |
| 2003/0093061 A1 | 5/2003 | Ganem | 604/533 |

| | | | | | | |
|---|---|---|---|---|---|---|
| 2003/0098430 | A1 | 5/2003 | Leinsing et al. ......... 251/149.6 | WO | 96/00107 | 1/1996 |
| 2003/0141477 | A1 | 7/2003 | Miller ..................... 251/149.1 | WO | 97/39791 | 10/1997 |
| 2004/0073171 | A1 | 4/2004 | Rogers et al. ......... 604/164.13 | WO | 98/22178 | 5/1998 |
| | | | | WO | 98/26835 | 6/1998 |
| | | | | WO | 98/39594 | 9/1998 |

FOREIGN PATENT DOCUMENTS

| | | |
|---|---|---|
| EP | 0629418 A1 | 12/1994 |
| EP | 1243285 | 9/2002 |
| GB | 2 079 162 | 1/1982 |
| GB | 01/20218 A1 | 3/2001 |
| WO | 83/02559 | 8/1983 |
| WO | 93/11828 | 6/1993 |
| WO | 00/44433 | 8/2000 |
| WO | WO 03/018104 A2 | 3/2003 |
| WO | WO 03/018105 A1 | 3/2003 |
| WO | WO 2004/060466 | 7/2004 |

* cited by examiner

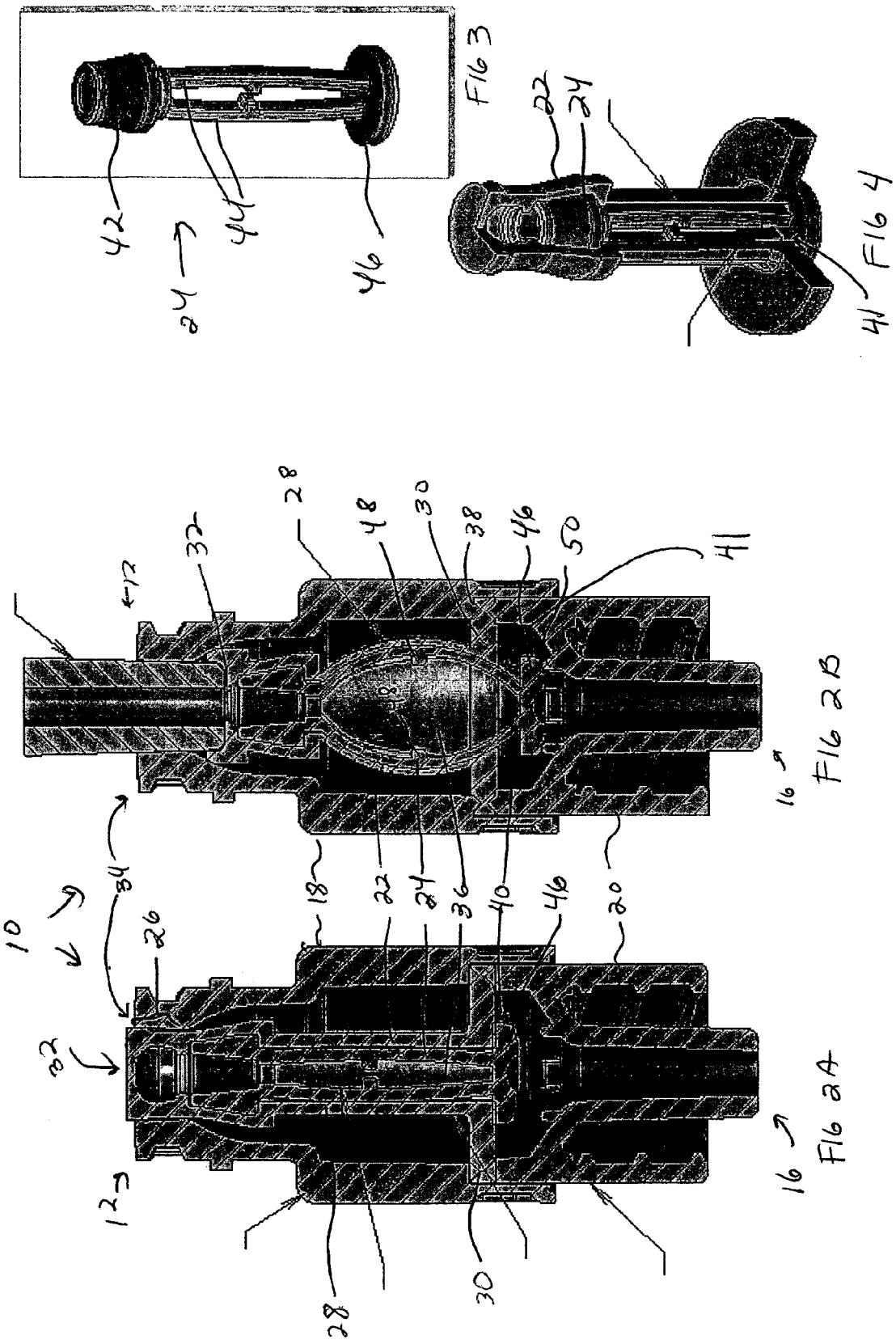

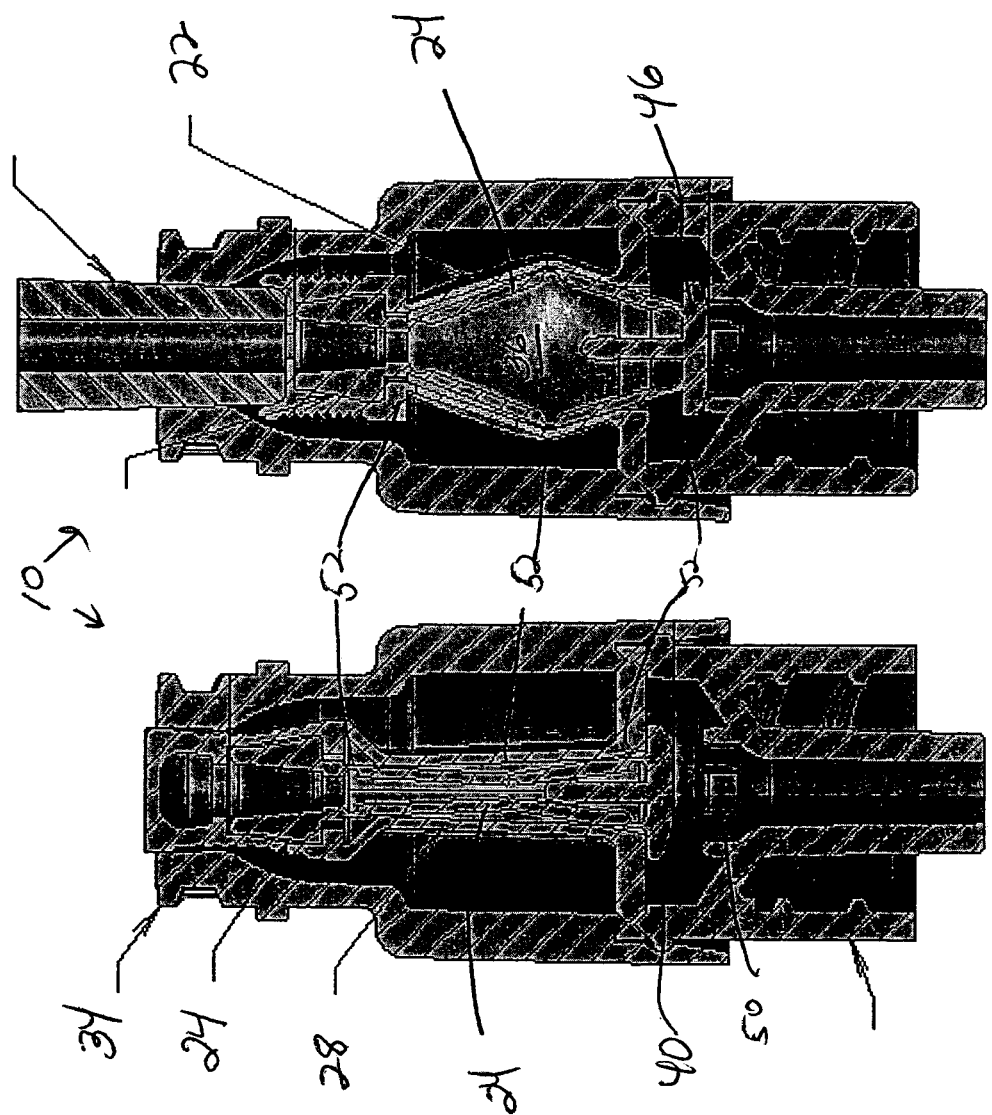

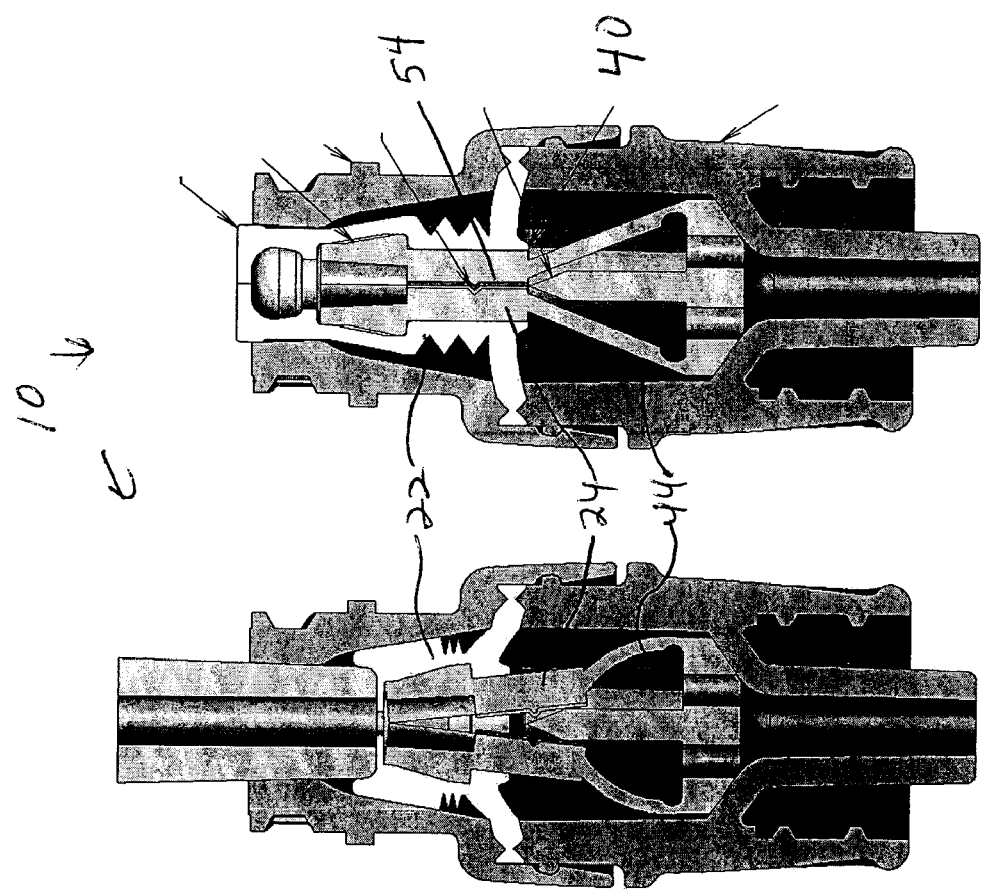

POSITIVE PUSH MEDICAL VALVE WITH INTERNAL SEAL

PRIORITY

This patent application claims priority from provisional U.S. patent application No. 60/422,074, filed Oct. 29, 2002, entitled, "POSITIVE PUSH MEDICAL VALVE WITH INTERNAL SEAL," and naming Brian L. Newton and Andrew L. Cote. as inventors, the disclosure of which is incorporated herein, in its entirety, by reference.

CROSS REFERENCE TO RELATED APPLICATIONS

This application is related to the following U.S. provisional and non-provisional patent applications, the disclosures of which are incorporated herein, in their entireties, by reference:
- application Ser. No. 09/479,327 (Bromberg & Sunstein LLP);
- application Ser. No. 09/812,237 (Bromberg & Sunstein LLP);
- application Ser. No. 10/007,377 (Bromberg & Sunstein LLP);
- Application No. 60/350,775 (Bromberg & Sunstein LLP); and
- application Ser. No. 10/224,299 (Bromberg & Sunstein LLP).

FIELD OF THE INVENTION

The invention generally relates to medical products and, more particularly, the invention relates to devices for reducing backflow through a medical valve.

BACKGROUND OF THE INVENTION

In general terms, medical valving devices often act as a sealed port that may be repeatedly accessed to non-invasively inject fluid into (or withdraw fluid from) a patient's vasculature. Consequently, a medical valve permits the patient's vasculature to be freely accessed without requiring such patient's skin be repeatedly pierced by a needle.

Medical personnel insert a syringe into the medical valve to inject fluid into (or withdraw fluid from) a patient who has an appropriately secured medical valve. Once inserted, fluid may be freely injected into or withdrawn from the patient. Problems arise, however, when the syringe is withdrawn from the valve. Specifically, a back pressure (i.e., a proximally directed pressure) produced by the withdrawing syringe undesirably can cause blood to leak proximally into the valve. In addition to coagulating and impeding the mechanical operation of the valve, blood in the valve also compromises the sterility of the valve.

SUMMARY OF THE INVENTION

In accordance with one aspect of the invention, a medical valve having an open mode to permit fluid flow and a closed mode to prevent fluid flow has a body and a valving element within the interior of the body. The body also has a valving element within its interior, and proximal and distal ports. The valving element controls fluid flow between the proximal and distal ports. Moreover, the valving element includes a resilient member and a plug. The resilient member forms a variable sized fluid chamber within the interior of the body, while the plug cooperates with the gland to provide an internal seal (within the interior of the body) that is spaced from the proximal port. The plug is capable of radially expanding the resilient member when the valve transitions from the closed mode to the open mode. The fluid chamber has a larger volume when in the open mode than when in the closed mode.

In some embodiments, the resilient member forms a proximal seal at the proximal port. In addition, the plug may include a plurality of legs that bow outwardly upon application of a distally directed force. The plurality of legs may normally bow outwardly, and/or the plug may have and a leg separator to prevent contact of the legs.

The interior may have a stop, where the plug is capable of longitudinally moving distally within the interior to contact the stop. The plug is capable of radially expanding the resilient member after the plug contacts the stop. In some embodiments, the plug includes a distal end having a base. In such embodiment, the resilient member has an open distal end, and the plug distal end cooperates with the resilient member open distal end to form the internal seal. The internal seal is closed when the resilient member open distal end is occluded by the plug distal end.

In accordance with another aspect of the invention, a medical valve includes a variable volume fluid chamber that is larger when the valve is in the open mode than when in the closed mode. Such valve also includes an internal seal. To these ends, the valve includes a body forming an interior, a proximal port, and a distal port. The valve also has a valving element within the interior of the body. The valving element controls fluid flow between the proximal and distal ports. A variable volume fluid chamber within the interior of the body has a larger volume when in the open mode than when in the closed mode. The valving element also includes an internal seal within the interior of the body. The internal seal is spaced from the proximal port.

In some embodiments, the valving element also includes a proximal seal that is spaced from the internal seal. The proximal seal may be swabbable.

BRIEF DESCRIPTION OF THE DRAWINGS

The foregoing and advantages of the invention will be appreciated more fully from the following further description thereof with reference to the accompanying drawings wherein:

FIG. 3 schematically shows a plug used in the valve shown in FIGS. 2A and 2B.

FIG. 4 schematically shows a cut-away view of the gland and plug of the valve shown in FIGS. 2A and 2B.

DESCRIPTION OF ILLUSTRATIVE EMBODIMENTS

In illustrative embodiments of the invention, a medical valve is configured to substantially eliminate fluid drawback when a nozzle or syringe is withdrawn from it. In fact, in some embodiments, the valve is expected to produce a positive, distally directed pressure when a nozzle or syringe is withdrawn. Such pressure necessarily should prevent non-negligible amounts of fluid from being drawn into the valve. Moreover, illustrative embodiments also include an internal seal.

To these ends, illustrative embodiments of the medical valve have an interior fluid chamber that is larger when it is in an open mode (i.e., permitting fluid flow, also referred to as "open position"), than when it is in a closed mode (i.e., preventing fluid flow, also referred to as "closed position"). More specifically, the fluid chamber is formed from a resilient member that, when transitioning from the closed mode toward the open mode, expands from its normal (i.e., relaxed) state. This expansion consequently increases the volume of fluid that the fluid chamber can contain when in the open mode. Accordingly, when retracting back to the closed mode, the resilient member returns to its normal state, which has a smaller volume. Excess fluid within the fluid chamber thus is forced out the distal end of the valve as the valve transitions toward the closed mode. Accordingly, fluid should not be drawn into the valve when withdrawing a syringe. Details of illustrative embodiments are discussed below.

Figure 1:
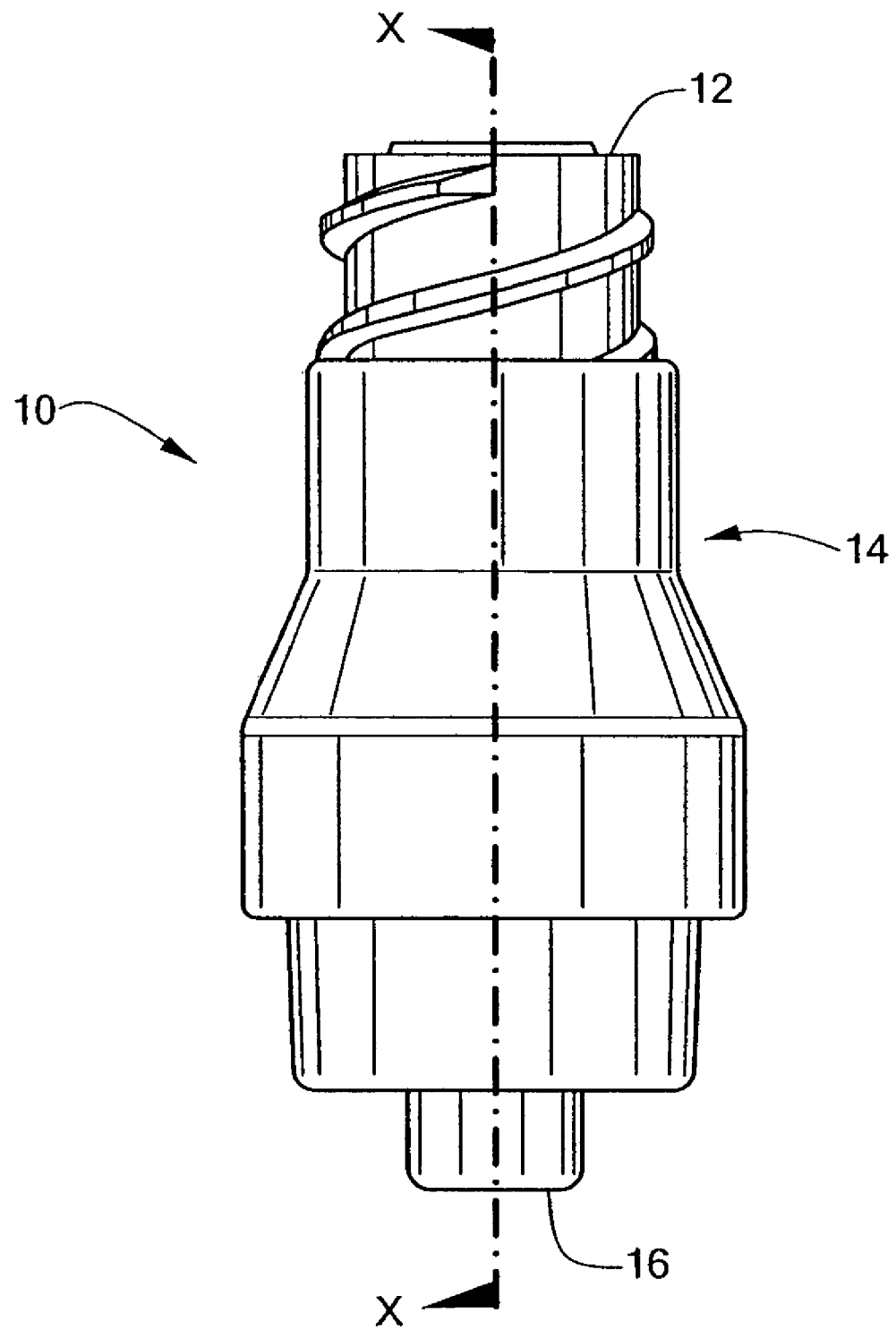
FIG. 1 schematically shows a medical valve configured in accordance with illustrative embodiments of the invention.

FIG. 1 schematically shows a medical valve 10 that is configured to reduce fluid drawback (a/k/a "back-flow," noted above) when a syringe or other type of nozzle is withdrawn from it. The valve 10 includes a proximal port 12 (also referred to herein as "inlet 12") for receiving the nozzle, a valve body/housing 14 having a valve element (different embodiments are shown in FIGS. 2–7) that controls fluid flow through the valve 10, and a distal port 16 (also referred to herein as outlet 16) for directing fluid between the valve 10 and a patient. The fluid preferably is in liquid form, such as liquid medication, to pass through a centrally formed fluid channel (discussed in greater detail below). Although much of the discussion herein refers to the proximal port 12 as a fluid inlet, and the distal port 16 as a fluid outlet, the proximal and distal ports 12 and 16 also may be respectively used as outlet and inlet ports.

In illustrative embodiments, the valve 10 is similar to the swab valve disclosed in U.S. Pat. No. 6,039,302 entitled, "SWABBABLE LUER-ACTIVATED VALVE," the disclosure of which is incorporated herein, in its entirety, by reference. Of course, various embodiments may relate to other non-swab valves and thus, such embodiments are not limited to swab valves.

Figure 2A:
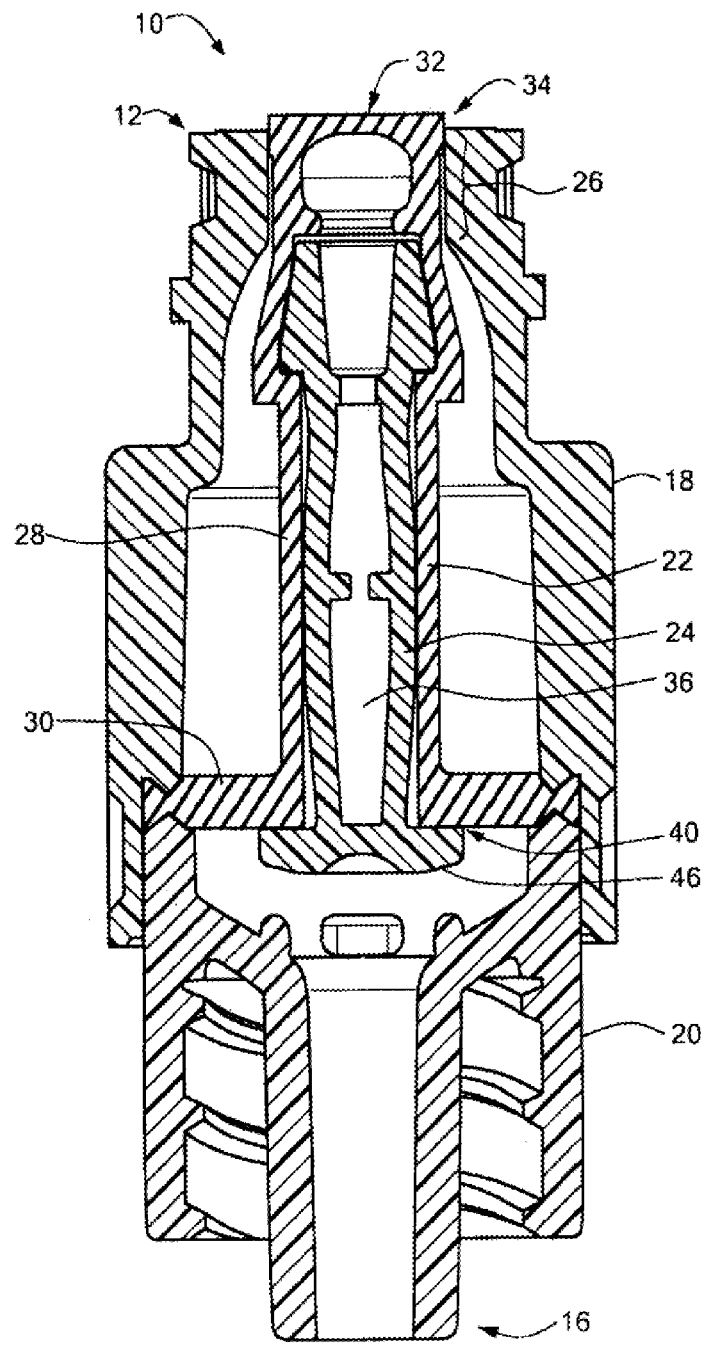
FIG. 2A schematically shows a cross-sectional view of a first embodiment of the valve shown in FIG. 1 in the closed position.
Figure 2B:
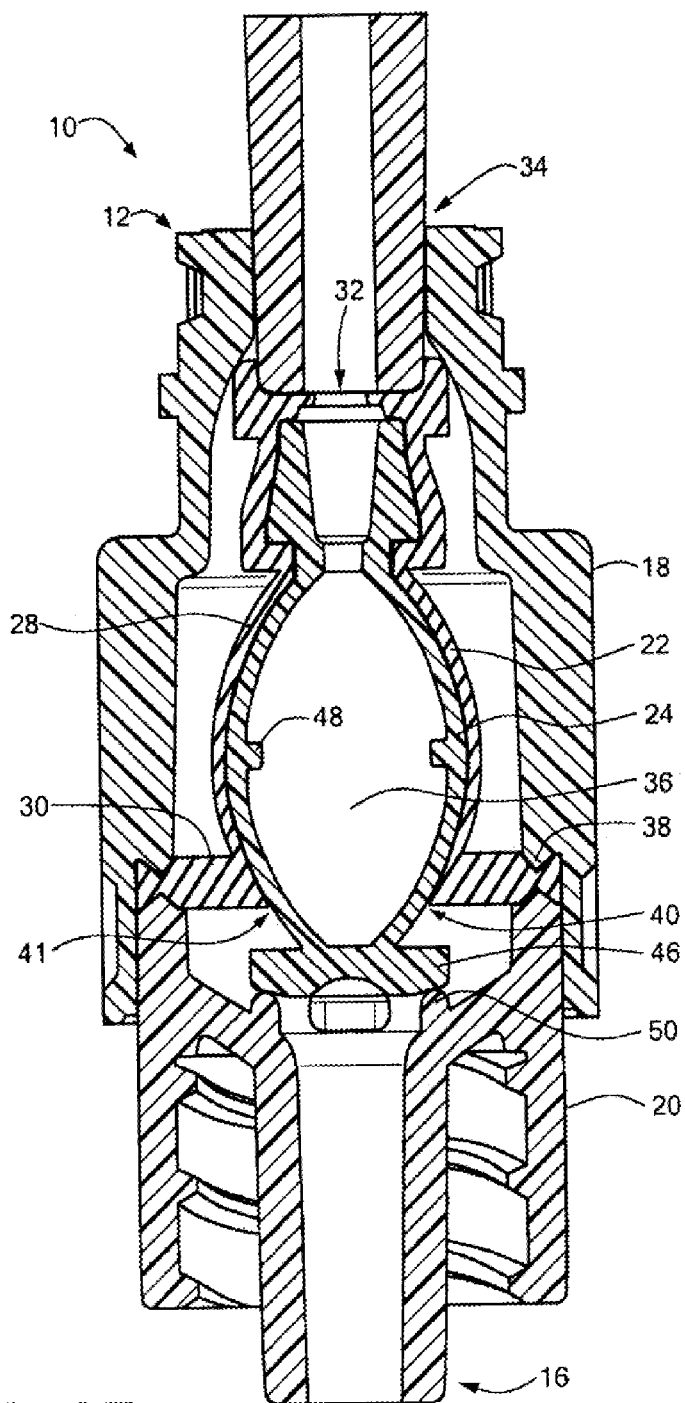
FIG. 2B schematically shows a cross-sectional view of the valve shown in FIG. 2A in the open position.

FIG. 2A schematically shows a cross-sectional view of a first embodiment of the medical valve 10 (shown in FIG. 1 along line X—X) in a closed mode. FIG. 2B similarly shows a cross-sectional view of the same valve 10, but in an open mode. In summary, the valve 10 includes four snap-fit components. Specifically, the valve 10 includes an inlet housing 18 having the inlet 12, and an outlet housing 20 having the outlet 16. The two housing portions 18 and 20 together form the valve body/housing 14. It should be noted that although some embodiments are discussed as being snap-fit components, various embodiments of the invention may be coupled by either snap-fit or other means, such as by ultrasonic welding. Accordingly, such embodiments are not intended to be limited to snap-fit components.

The remaining two components cooperate to valve fluid through the housing 14. Specifically, the valve 10 also has a stretchable, resilient, and compressible member (referred to in various embodiments herein as "gland 22") secured between the inlet housing 18 and outlet housing 20, and a longitudinally movable plug 24 (also more generally referred to as a "plug member" due in part to its plugging function) secured within the valve 10 by the gland 22.

The gland 22 is considered to have three contiguous sections that cooperate with the plug 24 to provide a valving function. In particular, those sections include 1) a proximally located swabbable seal section 26 to provide a low pressure, proximally located seal, 2) a tubular section 28 that cooperates with the plug 24 to provide a proximal bias to the plug 24, and 3) an attachment section 30 to secure the gland 22 within the valve 10 and cooperate with the plug 24 to provide the noted internal seal 40. Each of these sections are discussed below.

The seal section 26 has a normally closed aperture 32 to provide the above noted low pressure seal. Among other things, the aperture 32 may be, for example, a pierced hole or a slit. A nozzle or syringe thus may open the low pressure seal by deforming the seal section 26. Details of this deformation are discussed below.

The aperture 32 illustratively is formed to be normally closed when the gland 22 is not even mounted within the housing. No radial force thus is required by the housing to close the aperture 32. In fact, in some embodiments, the outer dimension of the seal section 26 is smaller than the inner dimension of the inlet 12. In alternative embodiments, however, the inner dimension of the inlet 12 is smaller than the outer dimension of the seal section 26 of the gland 22. Consequently, in such embodiments, the housing squeezes the seal section 26, thereby forcing the aperture 32 closed.

When the valve 10 is in the fully closed position, the seal section 26 is flush with, or extends slightly above, the exterior inlet face 34 of the housing. The seal section 26 and the exterior inlet face 34 thus present a swabbable surface. In other words, the seal section 26 and the exterior inlet face 34 may be easily wiped clean by any conventional means, such as with an alcohol swab. As mentioned in the above noted incorporated patent, valves having swabbable surfaces are known in the art as "swabbable valves." In other embodiments, however, the valve 10 is not a swabbable valve.

The second section of the gland 22, the tubular section 28, provides a number of functions. Primarily, the tubular section 28 is both resilient and compressible. Accordingly, the tubular section 28 effectively acts as a spring to normally maintain the gland 22 in the closed mode. Moreover, the tubular section 28 is radially expandable and contactable, thus providing the valve 10 with the noted anti-drawback capabilities. More specifically, the tubular section 28 forms an internal fluid chamber 36 that is a part of the fluid path within the valve 10. As discussed in greater detail below, the plug 24 radially expands the tubular section 28 as the valve 10 transitions from the closed position toward the open position. In a similar manner, the tubular section 28 contracts as the valve 10 transitions from the open position toward the closed position. Fluid thus should be forced out the distal port 16 as the volume of the tubular section 28 reduces toward its at rest volume.

In illustrative embodiments, the tubular section 28 of the gland 22 is formed to have a varying thickness. For example, the portions of the tubular section 28 being expanded may be thinner than those portions that are not being expanded. In some embodiments, the tubular section 28 actually may be rectangularly shaped, where a first pair of opposing walls are thinner than the other (second) pair opposing walls. The first pair of opposing walls permit the plug 24 to more easily expand the tubular section 28, while the second pair of opposing walls provide more structural strength to the overall gland structure.

The final one of the above listed gland sections, the attachment section 30, serves several important functions. Primarily, it at least partially secures the gland 22 within the housing. To that end, the attachment section 30 is secured between the inlet and outlet housings 18 and 20. To provide a more secure fit, the housing portions also include a pair of opposed annular upstanding ridges 38 that normally are forced into the proximal and distal surfaces of the attachment section 30. In addition, the attachment section 30 rests on a relatively flat inner surface of the housing, thus providing a base from which the tubular section 28 can provide its spring (i.e., proximal biasing) functionality.

The attachment section 30 also cooperates with the plug 24 to provide the noted internal seal 40. Specifically, the attachment section 30 has a distal opening 41 that normally is occluded by the plug 24. As more clearly shown in FIGS. 3 and 4, the plug 24 has a proximal portion 42 secured within the valve 10 by gland seal section 26, a pair of legs 44 extending distally from the proximal portion 42 and terminating at a distal base portion 46. The plug 24 is normally is biased so that, in the absence of a distally directed force, the distal base portion 46 of the plug 24 occludes fluid flow through the distal opening 41 of the attachment section 30.

The internal seal 40 is formed so that it can withstand relatively high pressures (e.g., those higher pressures that may occur during anticipated use, such as pressures greater than about 60 p.s.i.). To that end, the distal base portion 46 of the plug 24 is formed to have a geometry that is matched to that of the distal opening 41 of the attachment section 30. For example, the distal base portion 46 may have an outer diameter that is larger than the inner diameter of the distal opening 41 of the attachment section 30. In addition, the proximally facing surface of the distal base portion 46 should have a contour and shape that permits it to mate with the gland distal opening 41 to seal against high back pressures. Accordingly, due to the performance of the internal seal 40, it is not necessary for the low pressure seal (i.e., the aperture 32 through the seal section 26) to resist large back pressures. In some embodiments, however, the low pressure seal may be formed to also resist relatively high back pressures.

The legs 44 of the plug 24 illustratively are formed to be normally bowed outwardly. In addition, although not necessary, each leg 44 also may have an enlarged portion 48 to ensure that the two legs 44 do not inadvertently flex inwardly either when the valve 10 is actuated, and during assembly (i.e., when the plug 24 is inserted into the gland 22). The enlarged portions 48 normally contact each other. In alternative embodiments, only one leg 44 may have an enlarged portion 48. It should be noted that although only two legs 44 are discussed, other embodiments may have more than two legs 44. In some embodiments, the plug 24 may have only a single leg 44 that performs the same function of radially expanding the gland 22.

As shown in FIG. 2B, insertion of a nozzle (e.g., a blunt tip syringe) forces the seal section 26 of the gland 22 to collapse onto the proximally facing surface of the plug 24, thus opening the aperture 32. In addition, this force also causes the plug 24 to move distally within the valve 10 (against the proximal bias of the gland 22). This distal movement unseats the distal base portion 46 of the plug 24 from the distal opening 41 of the gland 22, thus opening the internal seal 40. Accordingly, when the internal seal 40 is open, the valve 10 is considered to have an open fluid channel extending between the proximal and distal ports 12 and 16.

The plug 24 moves distally until its distal base portion 46 contacts a stop 50 within the interior of the outlet housing 20. After the plug 24 contacts the stop 50, the legs 44 begin to bow outwardly as the nozzle applies more distally directed force. This bowing forces the tubular section 28 of the gland 22 to also expand, consequently expanding the internal fluid chamber 36 discussed above. Fluid from the nozzle thus may travel through the above noted fluid channel. Specifically, fluid flows through the aperture 32 and into the fluid chamber 36. From there, fluid travels though a distal channel formed by the outlet housing 20, and out through the distal port 16.

Removal of the distally directed force thus causes a similar, but opposite, effect. Specifically, the legs 44 begin moving radially inwardly, consequently reducing the volume of the internal chamber 36. Fluid remaining within the internal chamber 36 thus is forced distally through the distal port 16. After the legs 44 have retracted to their at-rest position (i.e., when not forced to bow radially outwardly), the plug 24 moves proximally until the internal seal 40 is reformed. In other words, the plug 24 moves proximally until the distal base portion 46 of the plug 24 reseats against the distal opening of the gland 22. The proximal seal also is completely resealed after the nozzle is removed from the valve 10.

In illustrative embodiments, the gland 22 is manufactured from a resilient elastomeric material, such as rubber or silicone. Other materials having similar properties may be used, however, so long as they can perform the functions discussed herein. The plug 24 illustratively is formed from a flexible and resilient plastic (e.g., polypropylene). Again, in a manner similar to the gland 22, other materials having similar properties may be used as long as they can perform the functions discussed herein.

Figure 5A:
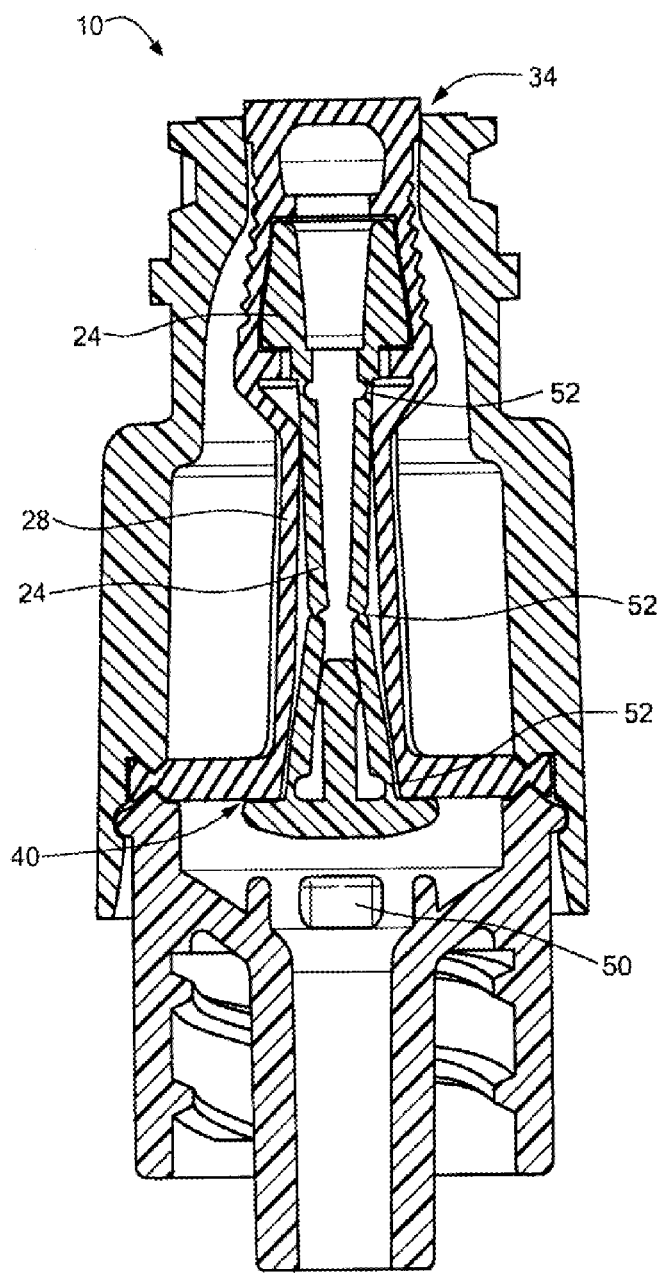
FIG. 5A schematically shows a cross-sectional view of a second embodiment of the valve shown in FIG. 1 in the closed position.
Figure 5B:
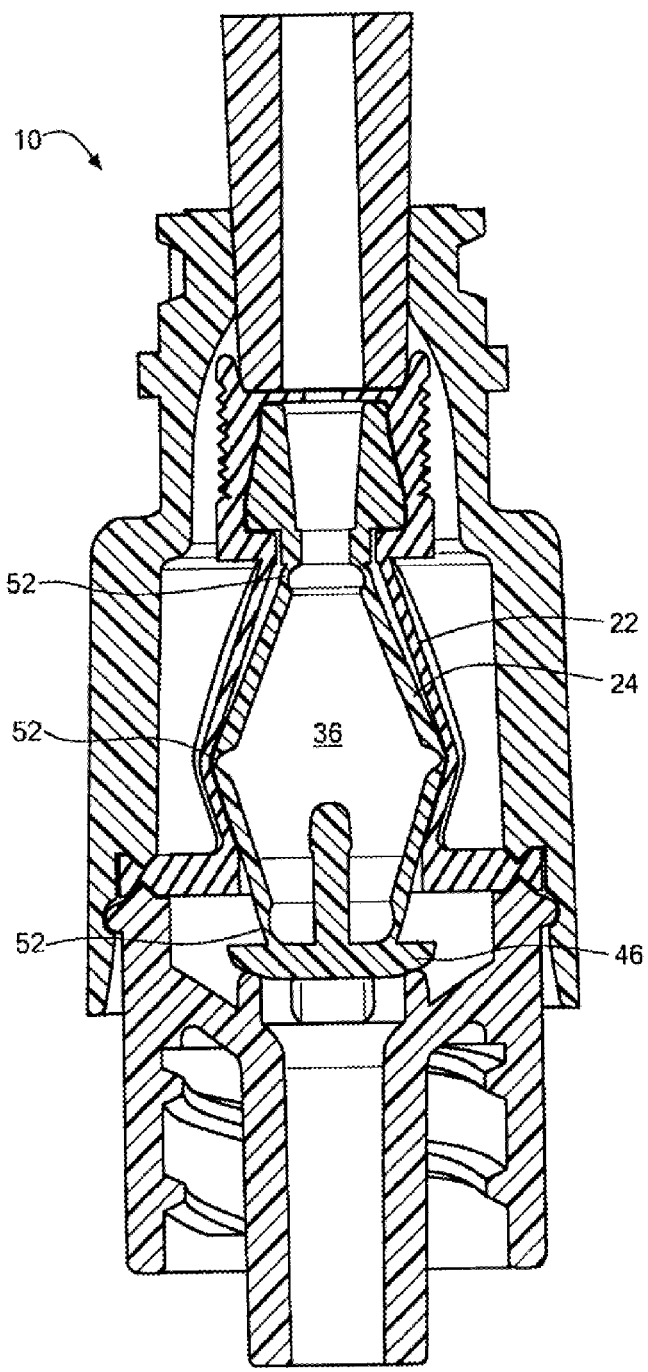
FIG. 5B schematically shows a cross-sectional view of the valve shown in FIG. 5A in the open position.

FIG. 5A schematically shows a cross-sectional view of a second embodiment of the medical valve 10 (shown in FIG. 1 along line X—X) in a closed mode. FIG. 5B similarly shows a cross-sectional view of the same valve 10, but in an open mode. This embodiment includes the same components as the first embodiment. The difference, however, is the shape and operation of the plug 24. In particular, each of the legs 44 of the plug 24 has three living hinge areas 52 to facilitate radial outward movement of the gland 22. In some embodiments, the legs 44 are normally bowed outwardly. In other embodiments, however, the legs 44 are not normally bowed outwardly. The plug 24 also includes a vertical member to ensure that the legs 44 to not bow inwardly when a distally directed force is applied. Also, in a manner similar to the embodiment shown in FIGS. 2A and 2B, the valve 10 also includes the internal high-pressure seal 40.

The seal section 26 of the gland 22 is shown in this embodiment as having an accordion-type structure. This structure relieves the seal section 26 when being forced to collapse. This feature is optional.

Operation of this embodiment is substantially similar to that of the embodiment shown in FIGS. 2A and 2B. Specifically, insertion of a nozzle (e.g., a blunt tip syringe)

forces the seal section 26 of the gland 22 to collapse onto the proximally facing surface of the plug 24, thus opening the aperture 32. In addition, this force also causes the plug 24 to move distally within the valve 10, consequently unseating the distal base portion 46 of the plug 24 from the distal opening of the gland 22.

The plug 24 moves distally until its distal base portion 46 contacts a stop 50 within the interior of the outlet housing 20. After the plug 24 contacts the stop 50, the legs 44 begin to bow outwardly as the nozzle applies more distally directed force. This bowing forces the tubular section 28 of the gland 22 to also expand, thus expanding the internal fluid chamber 36 discussed above.

Removal of the distally directed force thus causes a similar, but opposite, effect. Specifically, the legs 44 begin moving radially inwardly, consequently reducing the volume of the internal chamber 36. Fluid remaining within the internal chamber 36 thus is forced distally through the distal port 16. After the legs 44 have retracted to their at-rest position (i.e., when not forced to bow radially outwardly), the plug 24 moves proximally until the internal seal 40 is reformed. The proximal seal also is completely resealed after the nozzle is removed from the valve 10.

Figure 6A:
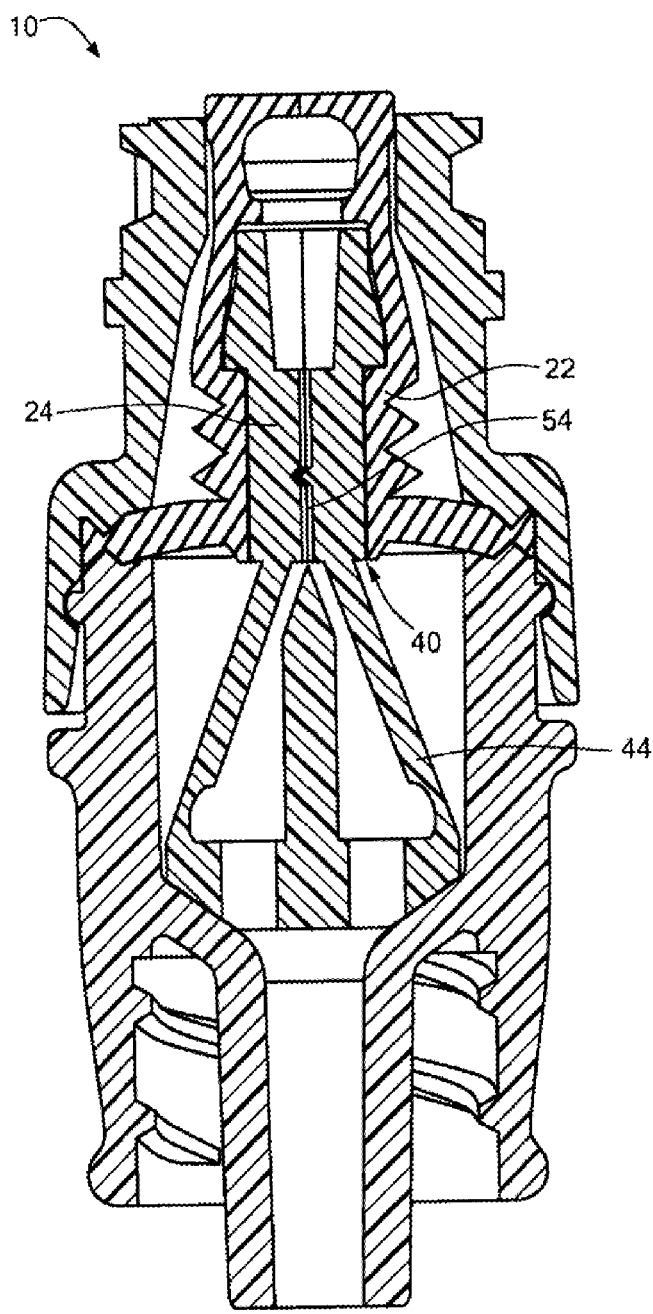
FIG. 6A schematically shows a cross-sectional view of a third embodiment of the valve shown in FIG. 1 in the closed position.
Figure 6B:
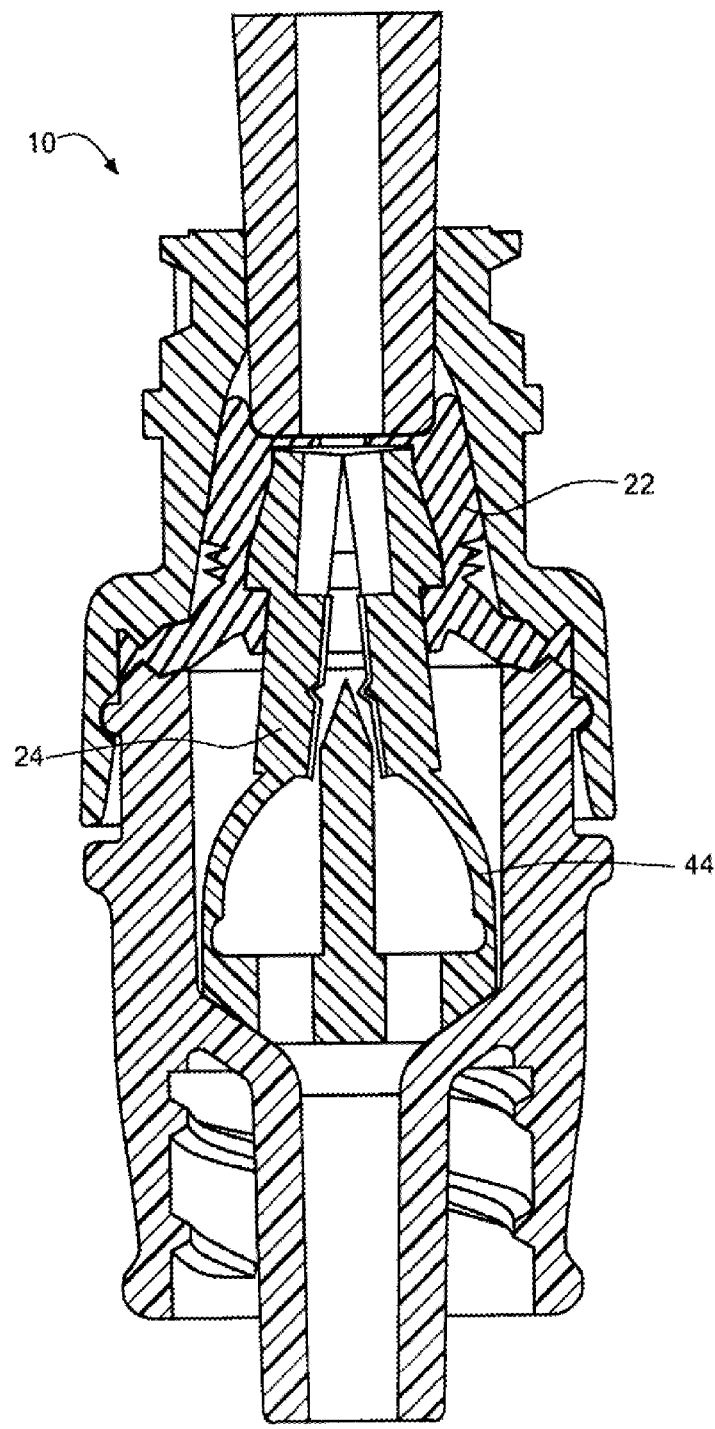
FIG. 6B schematically shows a cross-sectional view of the valve shown in FIG. 6A in the open position.
Figure 7:
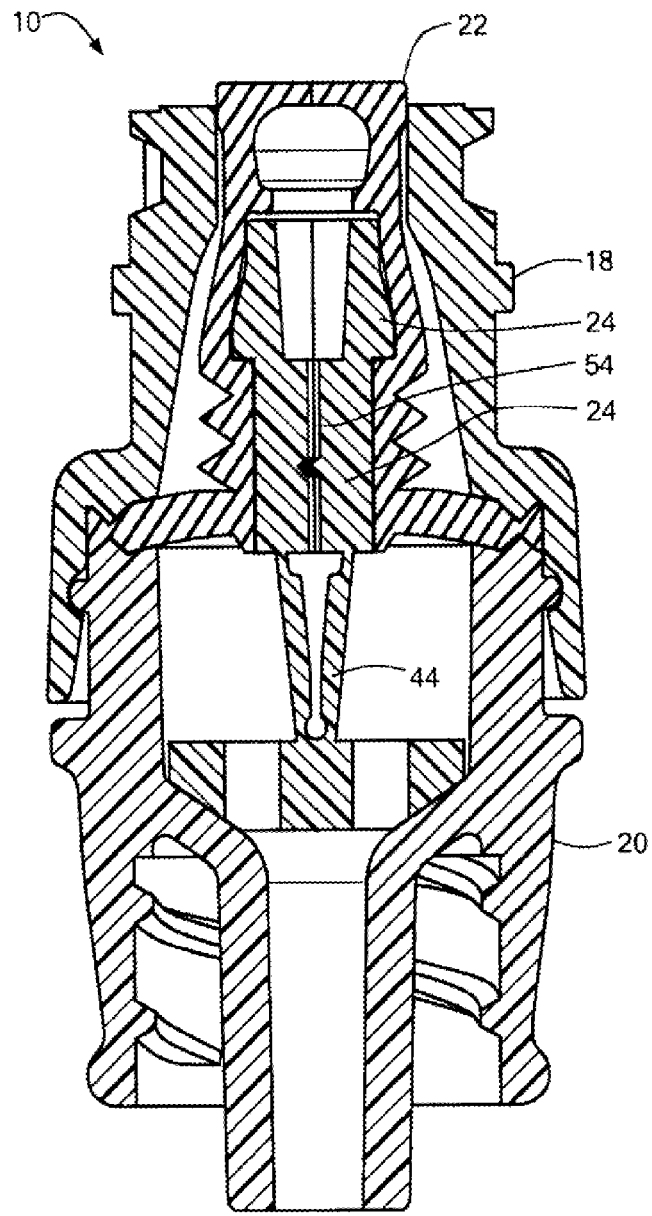

FIG. 6A schematically shows a cross-sectional view of a third embodiment of the medical valve 10 (shown in FIG. 1 along line X—X) in a closed mode. FIG. 6B similarly shows a cross-sectional view of the same valve 10, but in an open mode. This embodiment includes the same components as the first and second embodiments. In particular, this embodiment includes the inlet and outlet housing portions, the plug 24 and the gland 22.

The differences between this embodiment and the earlier mentioned embodiment is the configuration of the different components. In particular, the inlet and outlet housing portions meet to secure the gland attachment section 30 at a location that is proximal to that location on the first and second embodiments.

More significant, however, is the shape and operation of the plug 24. In particular, the plug 24 illustratively is split down its center and thus, separable. To that end, the plug 24 illustratively includes an occluded portion 54 that has two longitudinal plug sections normally flush against one another. When flush, as shown in FIG. 6A, this occluded portion 54 acts as the noted high pressure internal seal 40. The plug 24 also includes a pair of legs 44 normally in contact with the lower portion of the housing interior, and vertical member to ensure that the two housing halves separate when open.

As shown in FIGS. 6A and 6B, insertion of a nozzle forces the seal section 26 of the gland 22 to collapse onto the proximally facing surface of the plug 24, thus opening the aperture 32. The force also causes the legs 44 to bow radially outwardly, thereby permitting the two longitudinal plug sections to separate. This separation consequently expands the overall fluid volume within the valve 10, thus providing the desired anti-drawback functionality. Fluid thus flows through the proximal port 12, through the occluding portion 54 and valve interior, through holes at the base of the plug 24, and out the distal port 16.

Figure 7:
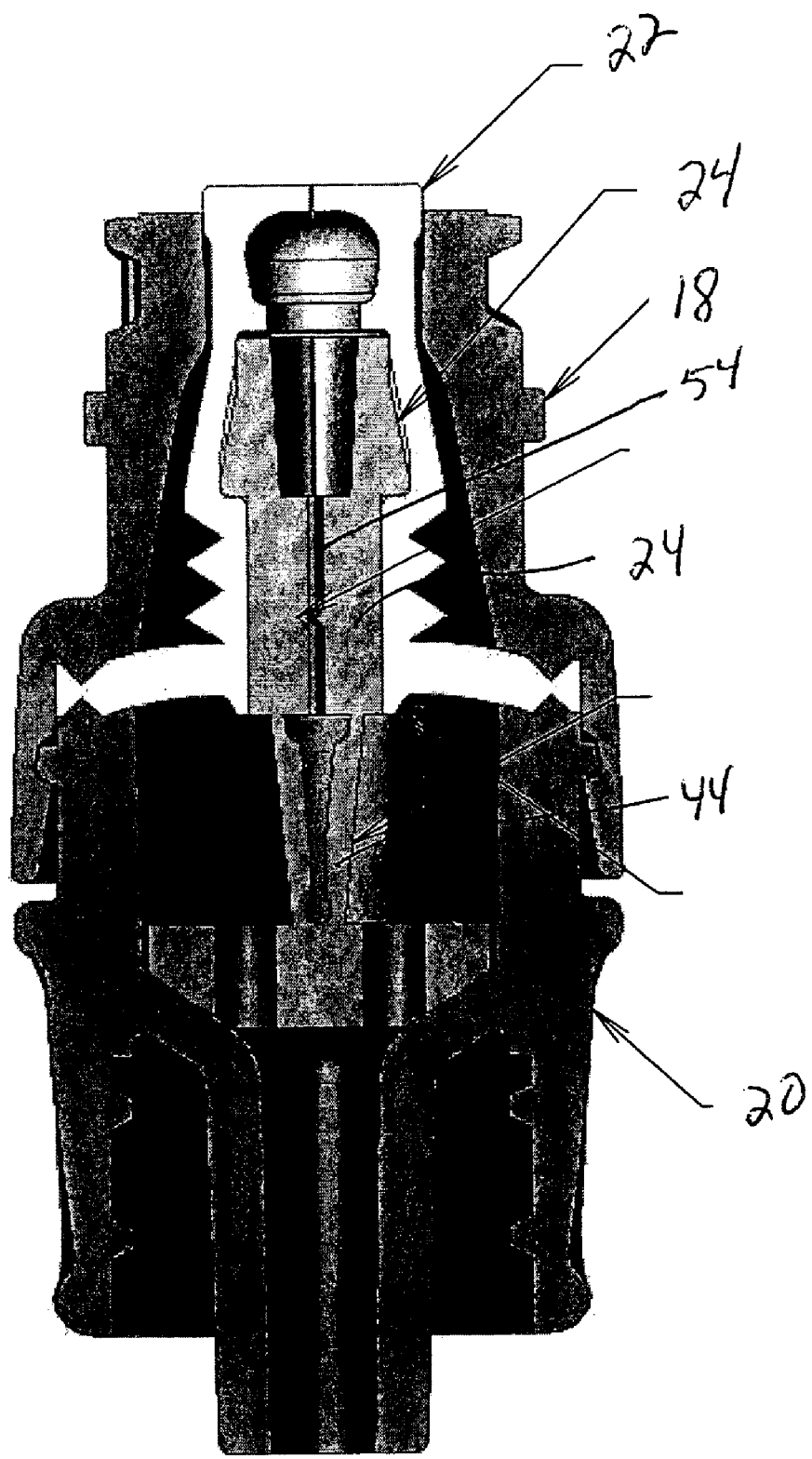
FIG. 7 schematically shows a cross-sectional view of a fourth embodiment of the valve shown in FIG. 1 in the closed position.
Figure 1:
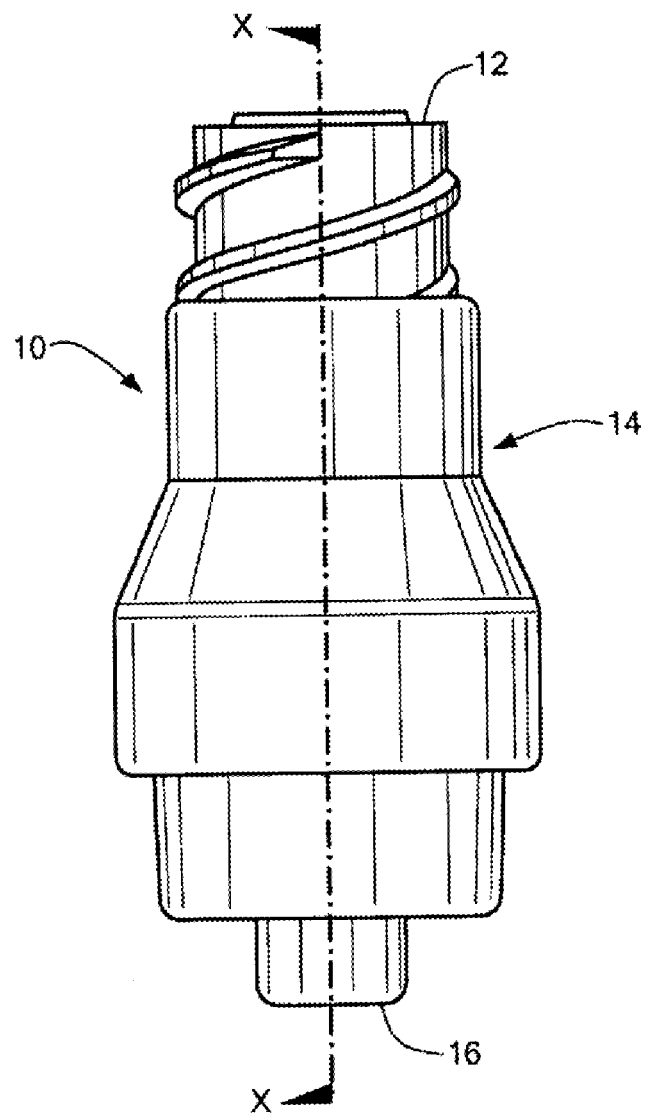

FIG. 7 schematically shows a cross-sectional view of a fourth embodiment of the valve 10 shown in FIG. 1. This embodiment is very similar to the third embodiment, except that it does not include the vertical member, and its legs 44 are normally tapered as they extend distally. Application of a distally directed force forces the two plug portions (of the occluding portion) to separate, consequently increasing the internal volume. Also in a manner similar to the previous embodiment, the occluding portion of the plug 24 acts as a high-pressure seal 40.

The plug 24 in both the third and forth embodiments illustratively may be formed to have a more pliable, sealing material on the plug portions that normally are flush. For example, a conventional two shot process may be used to apply an elastomeric layer to that surface. In illustrative embodiments, the entire plug 24 is formed to be a long strip of material that, during assembly, is folded into the form shown in FIGS. 5A–7.

It should be noted that measurements, other numbers, and various indicia on the figures not discussed are exemplary. Accordingly, various embodiments are not intended to be limited to such numbers and/or indicia.

Although various exemplary embodiments of the invention are disclosed above, it should be apparent to those skilled in the art that various changes and modifications can be made that will achieve some of the advantages of the invention without departing from the true scope of the invention.

What is claimed is:

1. A medical valve having an open mode to permit fluid flow and a closed mode to prevent fluid flow, the medical valve comprising:

a body forming an interior, a proximal port, and a distal port, the interior having a fluid channel between the proximal port and the distal port; and a valving element within the interior of the body, the valving element controlling fluid flow between the proximal and distal ports, the valving element including a resilient member and a plug, the resilient member forming a fluid chamber within the interior of the body, the fluid chamber being at least a part of the fluid channel, the plug cooperating with the resilient member to provide an internal seal within the interior of the body, the internal seal being spaced from the proximal port, the plug radially stretching the resilient member when the valve transitions from the closed mode to the open mode, the radial expansion causing the fluid chamber to have a larger volume when in the open mode than when in the closed mode, the radial expansion also causing the fluid channel to have a larger volume when in the open mode than when in the closed mode.

2. The medical valve as defined by claim 1 wherein the resilient member forms a proximal seal at the proximal port.

3. The medical valve as defined by claim 1 wherein the plug includes a plurality of legs that bow outwardly upon application of a distally directed force.

4. The medical valve as defined by claim 1 wherein the plug includes a plurality of legs that normally bow outwardly.

5. The medical valve as defined by claim 1 wherein the plug includes a plurality of legs and a leg separator to prevent contact of the legs.

6. The medical valve as defined by claim 1 wherein the interior includes a stop, the plug longitudinally moving distally within the interior to contact the stop, the plug radially expanding the resilient member after the plug contacts the stop.

7. The medical valve as defined by claim 1 wherein the plug includes a distal end, the resilient member having an open distal end, the plug distal end cooperating with the resilient member open distal end to form the internal seal.

8. The medical valve as defined by claim 7 wherein the internal seal is closed when the resilient member open distal end is occluded by the plug distal end.

9. The medical valve as defined by claim 1 wherein the valve element is swabbable.

10. A medical valve having an open mode to permit fluid flow and a closed mode to prevent fluid flow, the medical valve comprising:
  a body forming an interior, a proximal port, and a distal port, the interior having a fluid channel between the proximal port and the distal port;
  a valving element within the interior of the body, the valving element controlling fluid flow through the fluid channel between the proximal and distal ports; and
  a variable volume fluid chamber that is located within the interior of the body and is at least a part of the fluid channel, the fluid chamber and fluid channel having a larger volume when in the open mode than when the valve is in the closed mode; and
  a swabbable proximal seal that is spaced from the internal seal;
  the valving element including:
    an internal seal within the interior of the body, the internal seal being spaced from the proximal port; and
    a plug member at least in part within a resilient member, wherein the plug member radially stretches a wall of the resilient member as the valve transitions toward the open mode.

11. The medical valve as defined by claim 10 wherein the valving element includes a split plug member forming at least two portions with separable opposing faces, the opposing faces being substantially flush against each other when in the closed mode.

12. A medical valve having an open mode to permit fluid flow and a closed mode to prevent fluid flow, the medical valve comprising:
  a body forming an interior, a proximal port, and a distal port, the interior having a fluid channel between the proximal port and the distal port;
  valving means for controlling fluid flow between the proximal and distal ports; and
  a variable volume fluid chamber within the interior of the body, the fluid chamber being at least a part of the fluid channel, the fluid chamber and fluid channel having a larger volume when in the open mode than when the valve is in the closed mode,
  the valving means including internal seal means for sealing the valve within the interior of the body, the internal seal means being spaced from the proximal port.

13. The medical valve as defined by claim 12 wherein the valving means includes a swabbable seal means.

14. The medical valve as defined by claim 12 wherein the valving means includes a plug within an resilient member.

15. The medical valve as defined by claim 14 wherein the plug includes means for radially expanding the resilient member when the valve transitions to the open mode.

16. The medical valve as defined by claim 14 wherein the plug has a plurality of legs that bow outwardly upon application of a distally directed force.

17. The medical valve as defined by claim 10 wherein the resilient member forces fluid distally toward the distal port when the valve transitions toward the closed mode.

18. The medical valve as defined by claim 1, wherein:
  the valving element defines an opening; and
  the plug cooperates with the resilient member to provide the internal seal within the interior of the body to close the opening defined by the resilient member when the valve is in the closed mode.

19. The medical valve as defined by claim 1, wherein, when the valve transitions from the closed mode to the open mode, the plug radially stretches the resilient member by exerting a force on at least a portion of the inside of the fluid chamber.

* * * * *

UNITED STATES PATENT AND TRADEMARK OFFICE
CERTIFICATE OF CORRECTION

| | | |
|---|---|---|
| PATENT NO. | : 7,357,792 B2 | |
| APPLICATION NO. | : 10/687515 | |
| DATED | : April 15, 2008 | |
| INVENTOR(S) | : Brian L. Newton et al. | |

It is certified that error appears in the above-identified patent and that said Letters Patent is hereby corrected as shown below:

Please substitute old existing drawings with the new illustrating formal drawings Figures 1-7 that are attached with the title page drawing.

Signed and Sealed this

Thirtieth Day of December, 2008

JON W. DUDAS
*Director of the United States Patent and Trademark Office*

(12) United States Patent
Newton et al.

(10) Patent No.: US 7,357,792 B2
(45) Date of Patent: Apr. 15, 2008

(54) POSITIVE PUSH MEDICAL VALVE WITH INTERNAL SEAL

(75) Inventors: Brian L. Newton, Woonsocket, RI (US); Andrew L. Cote, Sr., Merrimack, NH (US)

(73) Assignee: Nypro Inc., Clinton, MA (US)

( * ) Notice: Subject to any disclaimer, the term of this patent is extended or adjusted under 35 U.S.C. 154(b) by 206 days.

(21) Appl. No.: 10/687,515

(22) Filed: Oct. 16, 2003

(65) Prior Publication Data
US 2004/0133317 A1 Jul. 8, 2004

Related U.S. Application Data

(60) Provisional application No. 60/422,074, filed on Oct. 29, 2002.

(51) Int. Cl.
*A61M 39/00* (2006.01)

(52) U.S. Cl. .............. 604/244; 604/247; 604/256

(58) Field of Classification Search ......... 604/99.04, 604/246, 207, 206, 205, 202, 244, 256, 200, 604/201, 247; 251/149, 149.1
See application file for complete search history.

(56) References Cited

U.S. PATENT DOCUMENTS

| | | | |
|---|---|---|---|
| 2,594,405 A | 4/1952 | Deters | 137/83 |
| 2,693,801 A | 11/1954 | Foreman | 128/214 |
| 2,705,501 A | 4/1955 | Frizsch et al. | 137/313 |
| 2,756,740 A | 7/1956 | Deane | 128/1 |
| 2,899,975 A | 8/1959 | Fernandez | 137/543.17 |
| 2,999,499 A | 9/1961 | Willett | 128/214 |
| 3,087,492 A | 4/1963 | Garth | 128/350 |
| 3,105,511 A | 10/1963 | Murphy, Jr. | 137/399 |
| 3,192,949 A | 7/1965 | De Soto | 137/540 |
| 3,385,301 A | 5/1968 | Harautuneian | 128/349 |
| 3,399,677 A | 9/1968 | Gould et al. | 128/349 |
| 3,416,567 A | 12/1968 | Von Dardel et al. | 137/604 |
| 3,506,005 A | 4/1970 | Gilio et al. | 128/214 |
| 3,538,950 A | 11/1970 | Porteners | 137/608 |
| 3,570,484 A | 3/1971 | Steer | 128/214 |
| 3,572,375 A | 3/1971 | Rosenberg | 137/512 |

(Continued)

FOREIGN PATENT DOCUMENTS

EP 0268480 A1 5/1988

(Continued)

*Primary Examiner*—Nicholas D. Lucchesi
*Assistant Examiner*—Melissa A. McCorkle
(74) *Attorney, Agent, or Firm*—Bromberg & Sunstein LLP

(57) ABSTRACT

A medical valve having an open mode to permit fluid flow and a closed mode to prevent fluid flow has a body and a valving element within the interior of the body. The body also has a valving element within its interior, and a proximal port and a distal port. The valving element controls fluid flow between the proximal and distal ports. Moreover, the valving element includes a resilient member and a plug. The resilient member forms a variable sized fluid chamber within the interior of the body, while the plug cooperates with the gland to provide an internal seal (within the interior of the body) that is spaced from the proximal port. The plug is capable of radially expanding the resilient member when the valve transitions from the closed mode to the open mode. The fluid chamber has a larger volume when in the open mode than when in the closed mode.

19 Claims, 5 Drawing Sheets

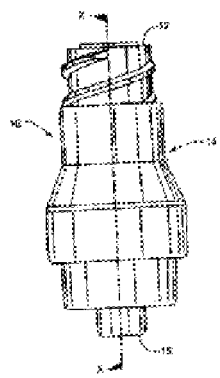

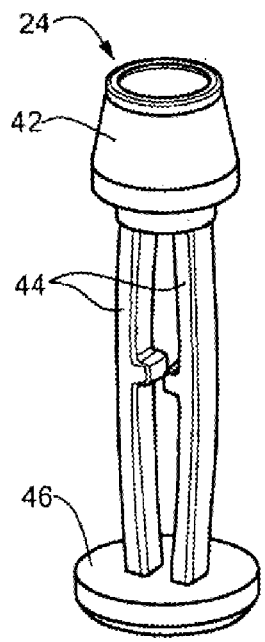
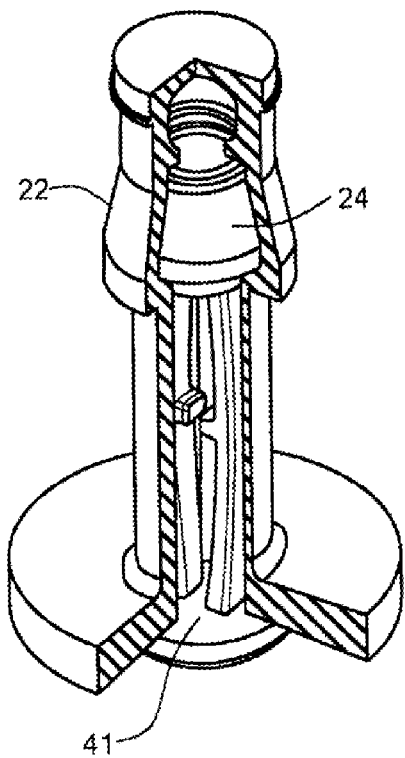
*FIG. 3*  *FIG. 4*